United States Patent
He et al.

(10) Patent No.: US 6,275,562 B1
(45) Date of Patent: Aug. 14, 2001

(54) APPARATUS AND METHODS FOR PERFORMING SCALABLE MULTISLICE COMPUTED TOMOGRAPHY SCAN

(75) Inventors: H. David He; Hui Hu, both of Waukesha; Holly A. McDaniel, New Berlin; Gary R. Strong, Waukesha, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/193,586

(22) Filed: Nov. 17, 1998

Related U.S. Application Data
(60) Provisional application No. 60/083,310, filed on Apr. 28, 1998.

(51) Int. Cl.[7] .................................................. A61B 6/00
(52) U.S. Cl. ................... 378/19; 378/4; 378/15; 378/20
(58) Field of Search .................. 378/4, 15, 19, 378/20, 150, 151

(56) References Cited

U.S. PATENT DOCUMENTS

| | | | |
|---|---|---|---|
| 4,965,726 | * 10/1990 | Heuscher et al. | 378/19 |
| 5,188,110 | * 2/1993 | Sugimoto | 600/425 |
| 5,291,402 | * 3/1994 | Pfoh | 378/13 |
| 5,430,783 | * 7/1995 | Hu et al. | 378/15 |
| 5,469,487 | 11/1995 | Hu | 378/9 |
| 5,513,236 | 4/1996 | Hui | 378/15 |
| 5,541,970 | 7/1996 | Hu | 378/4 |
| 5,559,847 | 9/1996 | Hu et al. | 378/4 |
| 5,606,585 | 2/1997 | Hu | 378/15 |
| 5,625,661 | * 4/1997 | Oikawa | 378/15 |
| 5,668,846 | * 9/1997 | Fox et al. | 378/4 |
| 5,684,855 | * 11/1997 | Aradate | 378/4 |
| 5,732,118 | * 3/1998 | Hsieh | 378/19 |
| 5,734,691 | * 3/1998 | Hu et al. | 378/4 |

(List continued on next page.)

FOREIGN PATENT DOCUMENTS

| | | |
|---|---|---|
| 198 53 646 A1 | 5/1999 | (DE) . |
| 0 981 999 A2 | 3/2000 | (EP) . |

*Primary Examiner*—David P. Porta
*Assistant Examiner*—Allen C. Ho
(74) *Attorney, Agent, or Firm*—Armstrong Teasdale LLP; Christian G. Cabou

(57) ABSTRACT

A scalable multislice system which, in one embodiment, includes a scalable multi-slice detector, a scalable data acquisition system (SDAS), scalable scan management, control, and image reconstruction processes, and scalable image display and analysis, is described. In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis. In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs. Such thinner slice images can be generated without rescanning the patient.

15 Claims, 7 Drawing Sheets

U.S. PATENT DOCUMENTS

| | | | |
|---|---|---|---|
| 5,828,719 | * 10/1998 | He et al. | 378/4 |
| 5,845,003 | * 12/1998 | Hu et al. | 382/131 |
| 5,864,598 | * 1/1999 | Hsieh et al. | 378/4 |
| 5,974,110 | * 10/1999 | Hu | 378/19 |
| 5,982,846 | * 11/1999 | Toth et al. | 378/19 |
| 6,023,494 | * 2/2000 | Senzig et al. | 378/4 |
| 6,039,047 | * 3/2000 | Rock et al. | 128/897 |
| 6,061,420 | * 5/2000 | Strong et al. | 378/4 |
| 6,081,576 | * 6/2000 | Schanen et al. | 378/19 |

* cited by examiner

| HELICAL | THICKNESS (mm) | | | | | |
|---|---|---|---|---|---|---|
| | 1.25 | 2.50 | 3.75 | *5.00* | *7.50* | *10.00* |
| | SCAN MODE | | | | | |
| | *HI-Q* | HI-SPEED | | | | |
| | SPEED (mm/rot) | | | | | |
| | 3.75 | *7.50* | *11.25* | *15.00* | 22.50 | 30.00 |
| AXIAL | THICKNESS (mm) | | | | | |
| | *1.25* | *2.50* | 3.75 | *5.00* | 7.50 | 10.00 |
| | NUMBER OF IMAGES PER ROTATION | | | | | |
| | 11 | *21* | *41* | | | |

FIG. 3

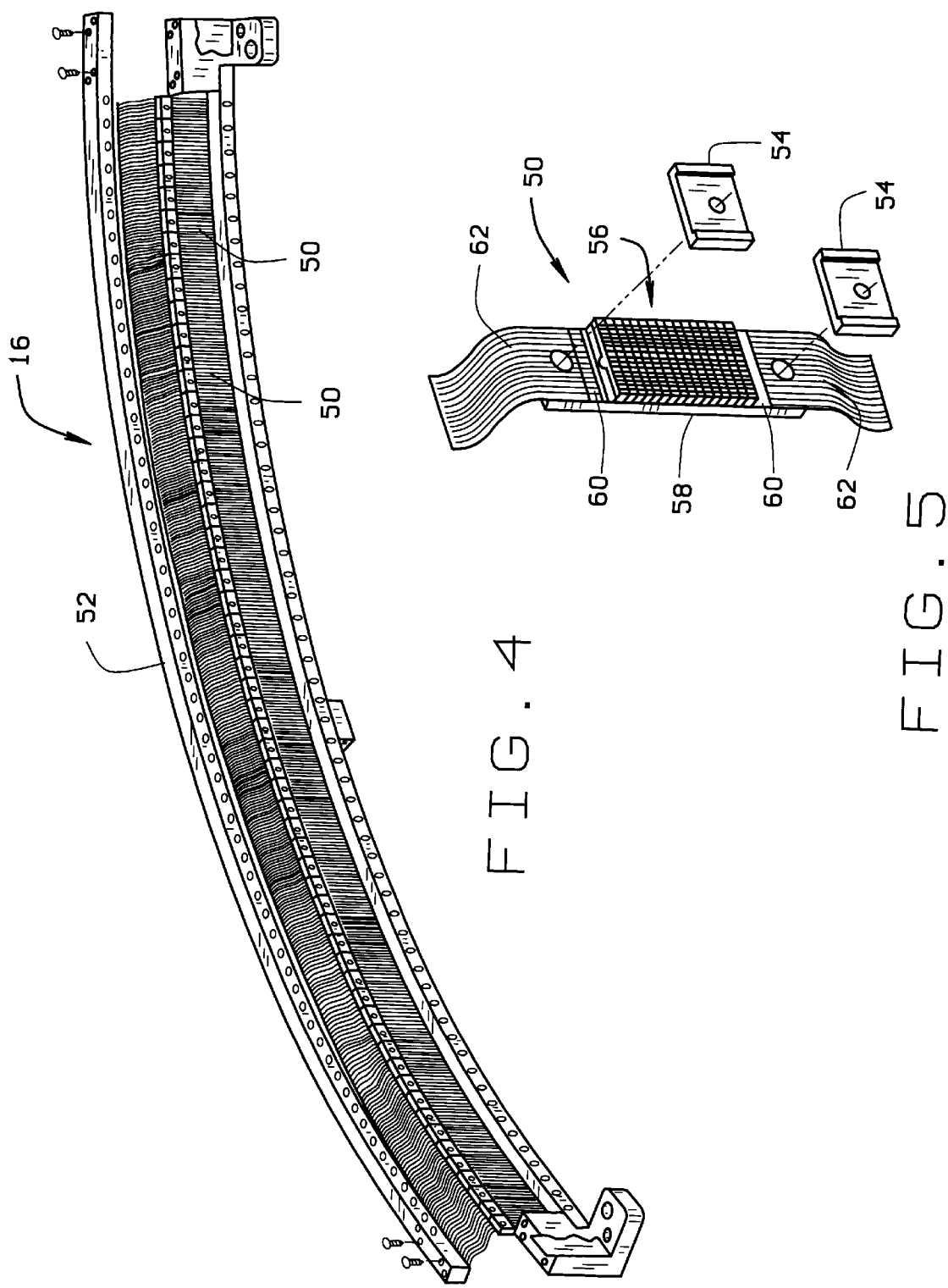

APPARATUS AND METHODS FOR PERFORMING SCALABLE MULTISLICE COMPUTED TOMOGRAPHY SCAN

CROSS REFERENCE TO RELATED APPLICATION

This application claims the benefit of U.S. Provisional Application No. 60/083310, filed Apr. 28, 1998.

BACKGROUND OF THE INVENTION

This invention relates generally to computed tomograph (CT) imaging and, more particularly, to a multi-slice CT scanner having a scalable x-ray collimator, x-ray detector, x-ray data acquisition system, scan data processing, and scan image reconstruction.

Typical CT patient scans are executed in either an axial mode (i.e., patient table stops, scan executed, and then patient table moves to next location) or in a helical mode (i.e., patient table moves continuously during the scan). Single slice scanners are common, and dual (two) slice CT systems are known. At least some of the commercially available dual slice systems have a number of limitations. Tradeoffs between patient scan speed, image quality, and x-ray tube loading generally must be made in performing such scans. For example, in order to obtain improved image quality, the patient scan speed may have to reduced or the x-ray tube loading must be increased, or both. Increasing patient scan speed may result in degraded image quality or require increased x-ray tube loading, or both. Until now, no known system provides the benefits of increased patient scan speed, improved image quality, and reduced x-ray tube loading.

Further, the known commercially available dual slice systems are not scalable in that such dual slice systems cannot be configured to collect more than two slices of data. Until now, no know system enables an operator to select for axial scans, the slice thickness and number of images per rotation, and for helical scans, the slice thickness, scan mode, and scan speed.

BRIEF SUMMARY OF THE INVENTION

These and other objects may be attained by a scalable multislice system which, in one embodiment, includes a scalable multi-slice detector, a scalable data acquisition system (SDAS), scalable scan management, control, and image reconstruction processes, and scalable image display and analysis. As used herein, the term scalable generally means that an operator can readily and simply select the desired number of slices and the slice thickness for images to be displayed. In the present multislice system, multiple rows of x-ray scan data can be acquired. In addition, increased patient scan speed, improved image quality, and reduced x-ray tube loading are achieved.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs. Such thinner slice images can be generated without rescanning the patient.

BRIEF DESCRIPTION OF THE DRAWINGS

FIG. 3 is an exemplary embodiment of a scan user interface than can be used in conjunction with the system illustrated in FIGS. 1 and 2.

FIG. 4 is a perspective view of a CT system detector array.

FIG. 5 is a perspective view of a detector module shown in FIG. 4.

DETAILED DESCRIPTION OF THE INVENTION

Figure 1:
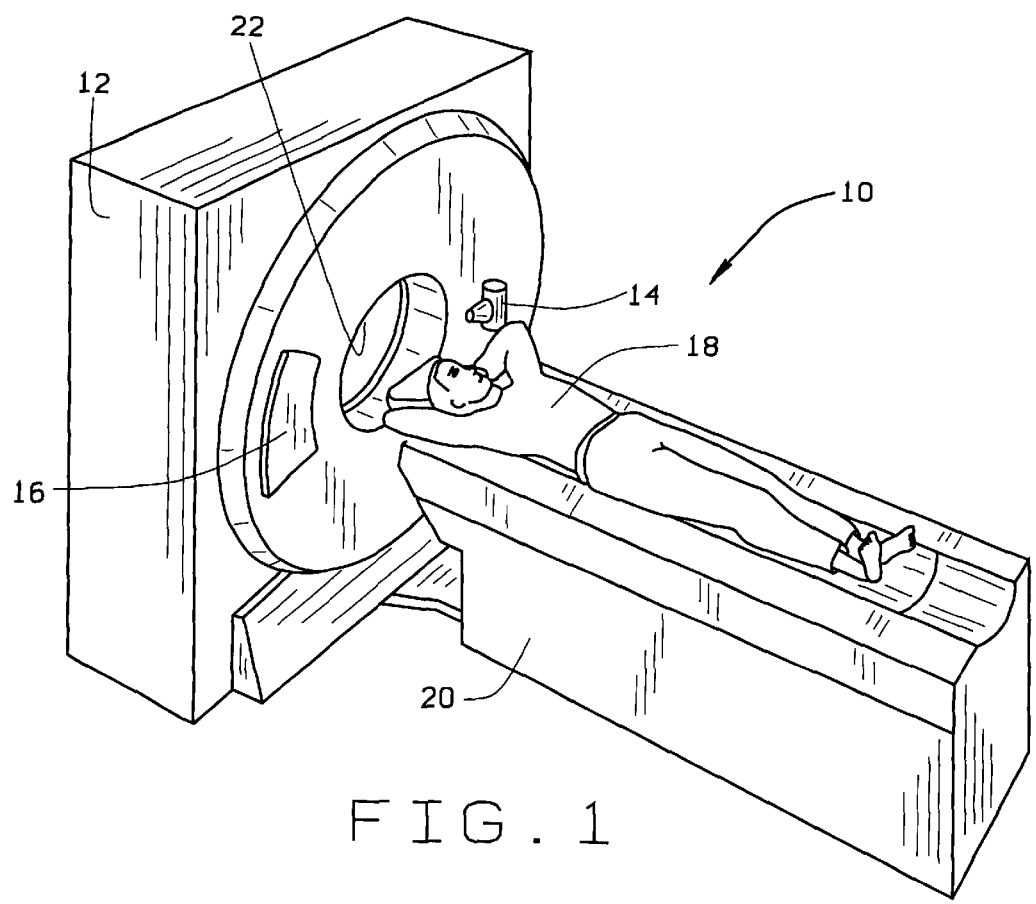
FIG. 1 is a pictorial view of a CT imaging system.

Referring to FIG. 1, a computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Set forth below is a description of the system hardware architecture, a description of the various scan modes, and a description of an exemplary user interface.

System Hardware Architecture

Figure 2:
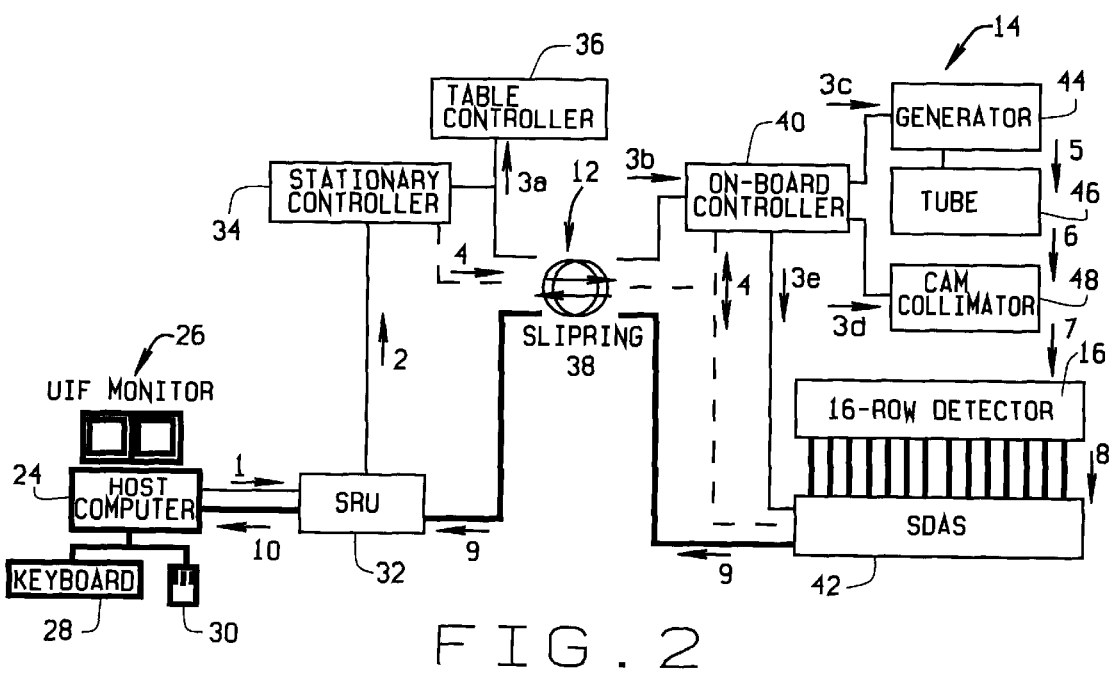
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 also include an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. A slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in the specific embodiment, includes forty eight interchangeable converter cards to support four row data acquisition. For two row data acquisition, twenty four cards could be used. In this specific embodiment, there are sixty four input channels per converter card and 1408 Hz sampling can be performed. SDAS 42 also includes a front-end pre-amplifier for amplifying the signals. A forward error correction is applied to the output data.

On-board controller 40 controls operation of x-ray source 14 and operation of SDAS 42, which converts analog signals to digital data as described above. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis. 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

With respect to operation of system 10, and in FIG. 2 data flow is illustrated by bold lines, control flow is illustrated by normal lines, and real-time control flow is illustrated by dotted lines. The numeric identifiers associated with the flows are set forth below.

1: scan and reconstruction prescription from operator
2: scan prescription to "master" controller
3: scan parameters distributed
3a: table position
3b: rotating parameters
3c: kV and mA selections
3d: x-ray beam collimation and filter selections
3e: detector slice thickness and SDAS gain selections
4: real-time control signals during scanning
5: high voltage
6: un-collimated x-ray beam
7: collimated x-ray beam
8: analog scan data
9: digital scan data
10: patient images Generally rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

Scan Modes

Generally, the above described CT system is operable to collect 1, 2 or more slices data. Axial and helical scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, and 5,606,585, and in co-pending U.S. patent application Ser. No. 08/561,382 (filed Nov. 21, 1995),Ser. No. 08/779,961 U.S. Pat. No. 5,828,719 (filed Dec. 23, 1996), and Ser. No. 08/797,101 U.S. Pat. No. 5,983,671 (filed Nov. 26, 1997), all of which are assigned to the present assignee, and all of which are incorporated herein, in their entirety, by reference.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis.

Exemplary axial multi-slice modes are set forth below in Table 1.

TABLE 1

| Acquisition Image Thickness & Mode | | Retrospective Reconstruction Image Thickness Available |
|---|---|---|
| 1.25 mm | 4i | 1.25, 2.5, 5 mm |
| 2.5 mm | 2i | 1.25, 2.5, 5 mm |
| 2.5 mm | 4i | 2.5, 5, 10 mm |
| 3.75 mm | 4i | 3.75, 7.5 mm |
| 5 mm | 1i | 1.25, 2.5, 5 mm |
| 5 mm | 2i | 2.5, 5, 10 mm |
| 5 mm | 4i | 5, 10 mm |
| 7.5 mm | 2i | 3.75, 7.5 mm |
| 10 mm | 1i | 2.5, 5, 10 mm |
| 10 mm | 2i | 5, 10 mm |

As one specific example, and for an axial mode acquisition for a 2.5 mm image thickness in the 2i mode, there are several retrospective reconstruction options that can be selected. For example, 4 images having a slice thickness of 1.25 mm can be reconstructed, 2 images having a slice thickness of 2.5 mm can be reconstructed, and 1 image having a slice thickness of 5 mm can be reconstructed. Accordingly, more images (e.g., 4 images) having a thinner slice thickness can be retrospectively reconstructed than the mode (i.e., 2i) in which the scan was performed. In addition, fewer images (e.g., 1 image) having a thicker slice thickness can be retrospectively reconstructed than the mode in which the scan was performed.

Further, and with respect to archiving images, the system enables storage of fewer images which require less storage space. For example, if 20 mm of patient anatomy is scanned in the 2i mode, 80 images can be generated. Storing 80 images for 20 mm of patient anatomy requires a large amount of memory. It is often the case that high resolution is not required for the entire 20 mm of patient anatomy. For example, it may be that only about 5 mm of the anatomy requires such high resolution. Using the data collected in 2.5 mm thickness 2i mode scan, the operator can retrospectively reconstruct images having a thickness of 5 mm for the majority of the anatomy, and thinner image slices (e.g., 1.25 mm) only at the locations where higher resolution is required. Using this retrospective reconstruction, the number of images to be archived can be significantly reduced.

The above described retrospective reconstruction is provided through the user interface and enabled because the scan data is collected using a multislice detector which is described below in more detail. With the thin slice scan data available, the operator can select from many different slice thicknesses when performing retrospective reconstruction.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs. Such thinner slice images can be generated without rescanning the patient.

Exemplary helical multi-slice modes are set forth below in Table 2.

TABLE 2

| Table Speed (mm / rotation) | | Retrospective Reconstruction |
|---|---|---|
| Hi-Q Scan Mode | Hi-Speed Scan Mode | Image Thicknesses Available |
| 3.75 | 7.5 | 1.25, 2.5 mm |
| 7.5 | 15 | 2.5, 3.75, 5 mm |
| 11.25 | 22.5 | 3.75, 5, 7.5 mm |
| 15 | 20 | 5, 7.5, 10 mm |

For example, in a high quality image (Hi-Q) scan mode of 3.75 mm/rotation (i.e., the patient table moves 3.75 mm for each gantry rotation), or in a high speed (Hi-Speed) scan mode of 7.5 mm/rotation, images having slice thicknesses of 1.25 mm and 2.5 mm can be reconstructed retrospectively. As with the axial multi-slice mode, many other alternatives are possible depending upon the particular construction of the system components. Again, such flexibility in retrospective reconstruction provides many advantages including enabling the generation of images having the necessary resolution yet reducing the memory necessary for storing the desired images.

Exemplary User Interface

FIG. 3 is an exemplary embodiment of a scan user interface than can be used in conjunction with the system illustrated in FIGS. 1 and 2. The interface would be implemented in an instruction set stored in host computer 24 (FIG. 2) and displayed on the host computer monitor. At the scan user interface, an operator can select the scan mode, i.e,. helical or axial, as well as the various scan parameter associated with each mode. The selections are made, for example, by the user by simply touching the desired area corresponding to the desired parameters. Touch sensitive interfaces are well known. Of course, many other types of interfaces could be used, and the interface illustrated in FIG. 3 is only an exemplary interface.

In the helical mode, the operator selects the desired slice thickness, the scan mode, and the scan speed. The "Hi-Q" scan corresponds to a high image quality scan and the "Hi-Speed" scan corresponds to a fast patient table speed, as described above in connection with Table 2. In the axial scan, the operator selects the desired slice thickness and the number of image to be generated per rotation.

Before now, no multi-slice CT system provides the scalable scan management, control, and image reconstruction processes, and scalable image display and analysis, as provided with the present system. With the present system, an operator can readily and simply select the desired number of slices and the slice thickness for images to be displayed. In addition, increased patient scan speed, improved image quality, and reduced x-ray tube loading are achieved.

Additional Component Details

Set forth below is a description of an exemplary scalable multislice CT system components in accordance with one embodiment of the present invention. Although specific component details are set forth below, it should be understood that many alternative embodiments are possible. For example, although one particular detector is described, other detectors could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis can be joined together in either direction to acquire scalable multislice scan data simultaneously, can be utilized.

Particularly, and referring to FIGS. 4 and 5, detector 16 includes a plurality of detector modules 50. Each detector module 50 is secured to a detector housing 52 by plates 54. Each module includes a multidimensional scintillator array 56 and a high density semiconductor array (not visible). A post patient collimator (not shown) is positioned over and adjacent scintillator array 56 to collimate x-ray beams before such beams impinge upon scintillator array 56. Scintillator array 56 includes a plurality of scintillation elements arranged in array, and the semiconductor array includes a plurality of photodiodes arranged in an identical array. The photodiodes are deposited, or formed on a substrate 58, and scintillator array 56 is positioned over and secured to substrate 58.

Switch and decoder apparatus 60 are coupled to the photodiode array. The photodiodes are optically coupled to scintillator array 56 and have electrical output lines for transmitting signals representative of the light output by scintillator array 56. Particularly, each photodiode produces a separate low level analog output signal that is a measurement of the beam attenuation for a specific scintillator of scintillator array 56. The photodiode output lines extend from opposing sides of the semiconductor, or photodiode, array and are connected (e.g., wire bonded) to respective apparatus 60.

Switch apparatus 60 is a multidimensional semiconductor switch array of similar size as the photodiode array, and switch apparatus 60 is coupled in electric circuit between the semiconductor array and SDAS 42 (FIG. 2). Apparatus 60, in one embodiment, includes a plurality of field effect transistors (FETs) arranged as a multidimensional array.

Each FET includes an input line electrically connected to one of the respective photodiode output lines, an output line, and a control line (not shown). FET output and control lines are electrically connected to SDAS 42 via a flexible electrical cable 62. Particularly, about one-half of photodiode output lines are electrically connected to each FET input line one side of the array with the other one-half of photodiode output lines electrically connected to the FET input lines on the other side of the array.

The decoder controls the operation of the FETs to enable, disable, or combine photodiode outputs in accordance with a desired number of slices and slice resolutions for each slice. The decoder, in one embodiment, is a decoder chip or a FET controller as known in the art, and the decoder includes a plurality of output and control lines coupled to the FETs and SDAS 42. Particularly, the decoder outputs are electrically connected to the switch apparatus control lines to enable the FETs to transmit the proper data. The decoder control lines are electrically connected to the FET control lines and determine which of the outputs will be enabled. Utilizing the decoder, specific FETs are enabled, disable, or have their outputs combined so that specific photodiode outputs are electrically connected to SDAS 42. Further details regarding detector 16 are set forth in co-pending U.S. patent application Ser. No. 08/978,805, Photodiode Array For A Scalable Multislice Scanning Computed Tomography System, which is assigned to the present assignee and hereby incorporated herein, in its entirety, by reference.

In one specific embodiment, detector 16 includes fifty-seven detector modules 50. The semiconductor array and scintillator array 56 each have an array size of 16×16. As a result, detector 16 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 16 may be operated in many different slice thickness and number modes, e.g., one, two, and four slice modes. For example, the FETs can be configured in the four slice mode so that data is collected for four slices from one or more rows of the photodiode array. Depending upon the specific configuration of the FETs as defined by decoder control lines, various combinations of photodiode outputs can be enabled, disabled, or combined so that the slice thickness may, for example, be 1.25 mm, 2.5 mm, 3.75 mm, or 5 mm. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
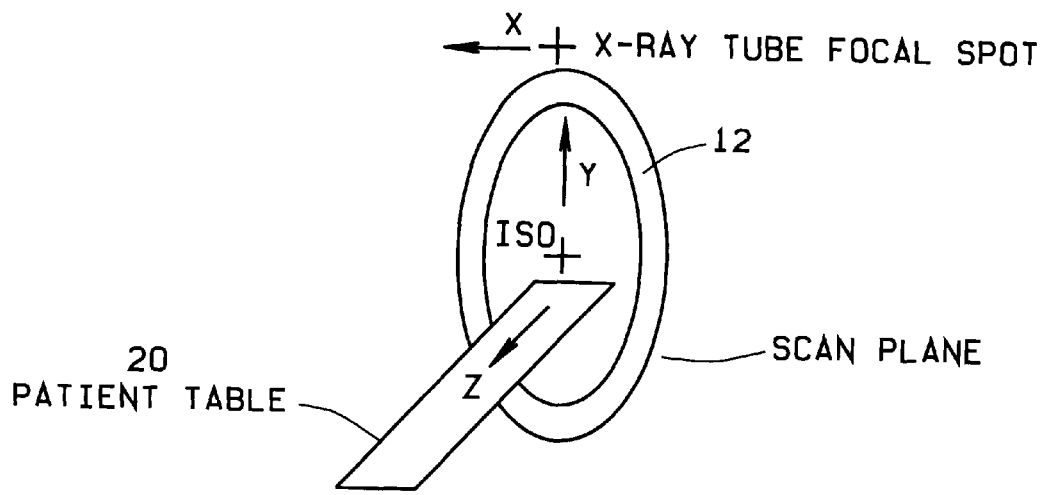
FIG. 6 illustrates the geometric configuration of the CT system illustrated in FIG. 1.

FIG. 6 illustrates the geometric configuration of the CT system illustrated in FIG. 1 and shows the gantry coordinate system. The coordinate system is referred to in the following figures and is provided only for explanation purposes. Particularly, the x-axis refers to an axis tangent to the circle of rotation of gantry 12. The y-axis refers to a radial axis extending from the iso center (ISO) of gantry 12 toward the x-ray tube focal spot. The z-axis is a longitudinal axis (in/out) with respect tot he scan plan. The patient is translated along the z-axis on patient table 20 during scanning.

Figure 7:
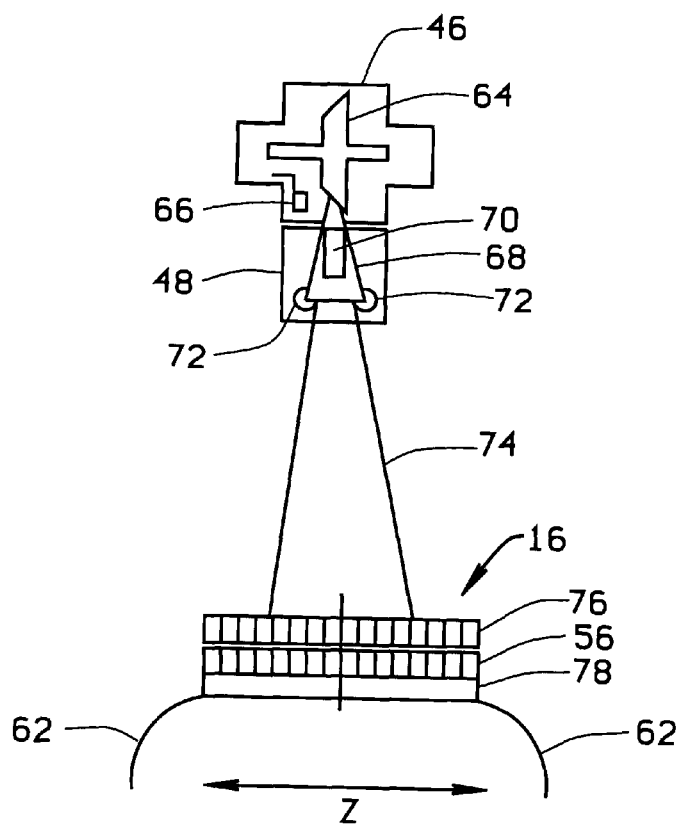
FIG. 7 is a schematic illustration of x-ray generation and detector components view from a side of the gantry.

Referring to FIG. 7, and in multislice scanning, data is collected at various z-axis locations. Particularly, FIG. 6 is a schematic illustration of system 10 viewed from a side of the gantry 12. X-ray tube 46 includes an anode/target 64 and a cathode 66. An uncollimated x-ray beam 68 is emitted by tube 46 and passes through cam collimator 48. Collimator 48 includes a bowtie filter 70 and tungsten cams 72. As explained in connection with FIG. 2, the position of cams 72 is controlled by an on-board controller 40 which receives its commands from host computer 24 via SRU 32 and stationary controller 34. Stepper motors, for example are connected to cams 72 for precisely controlling the position of cams 72. Cams 72 of cam collimator 48 can be independently adjusted with respect to the spacing between cams 72 and their location relative to the center of the collimator opening depending on the user selected data collection mode.

A collimated x-ray beam 74 is emitted from cam collimator 48, and beam 74 passes through patient 18 (FIG. 1) and impinges upon detector 16. As described above, detector 16 includes a collimator 76, a scintillator array 56, and a photodiode/switching array 78 (the photodiode and switching arrays are shown as one unit in FIG. 7 but may be separate arrays as described above). Outputs from array 78 are supplied, via a flex cable, to SDAS 42 for processing.

The following description relates to operation of cam collimator 48 and detector 16 for providing scalability in the number of slices and the slice thickness. Although the operation of cam collimator 48 and the operation of detector 16 are sometimes described separately herein, it should be understood that collimator 48 and detector 16 operate in combination to provide the desired number of slices and slice thickness.

Figure 8:
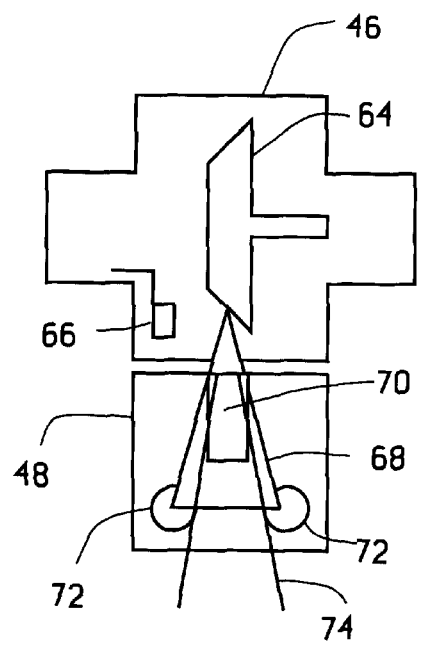
FIGS. 8, 9 and 10 illustrate operation of the cam collimator in the CT system illustrated in FIG. 1.
Figure 9:
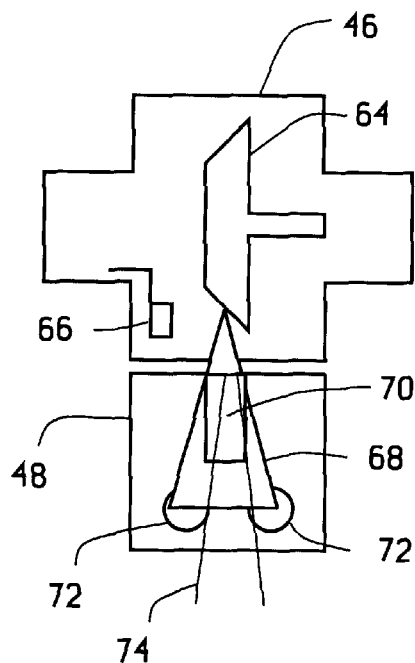
Figure 10:
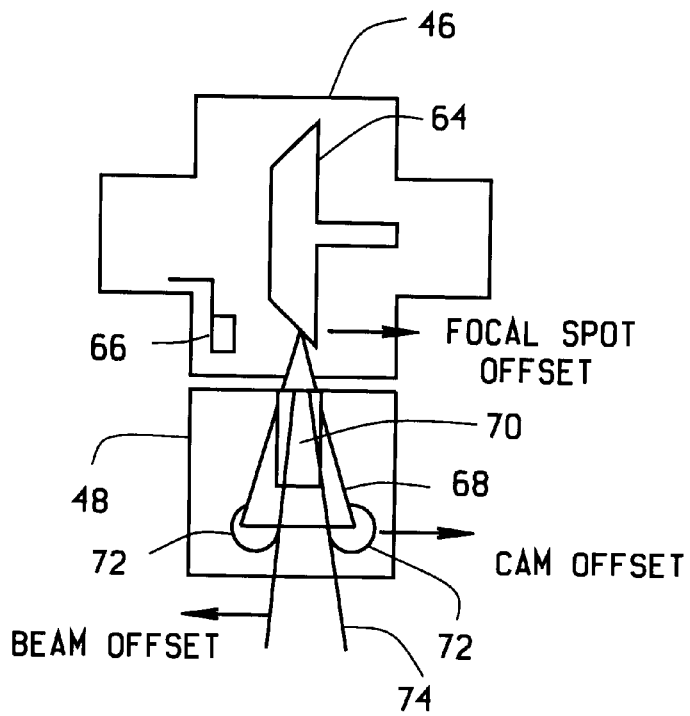

More specifically, FIGS. 8, 9, and 10 illustrate operation of cam collimator 48. FIG. 8 illustrates cam collimator 48 configured to emit a centered wide beam (e.g., a beam for obtaining 4 slices of data with a 5 mm slice thickness). For a narrow centered beam, and as shown in FIG. 9, cams 72 are moved inward an equal amount relative to a center of beam 68. For example, the cam collimator configured shown in FIG. 9 could be used for obtaining 4 slices of data with a 1.25 mm slice thickness.

Collimator 48 also can be used to adjust for z-axis beam offset which may occur during operation of tube 46. Particularly, and referring to FIG. 10, cams 72 can be positioned at unequal distances from the center of beam 68, as indicated by the arrow associated with the legend "cam offset". By offsetting cams 72 as shown in FIG. 10, beam 74 is offset as indicated by the arrow associated with the legend "beam offset".

As described below in more detail, by controlling the position and width of beam 74 at cam collimator 48, scans can be performed to obtain data for many different slice numbers and slice thicknesses. For example, FIG. 11 corresponds to a selected detector configuration when it is desired to obtain 4 slices of data with a slice thickness of 5.0 mm. Cams 72 are separated wide apart in the z-axis direction to provide 20 mm collimation, and the photodiode outputs are combined by switching array 78 into four separate slices. Particularly, each slice of data combines the outputs of four photodiodes into one signal (1A, 2A, 1B, and 2B), and each slice data signal (1A, 2A, 1B, and 2B) is supplied to SDAS 42 via flex cables 62.

Figure 11:
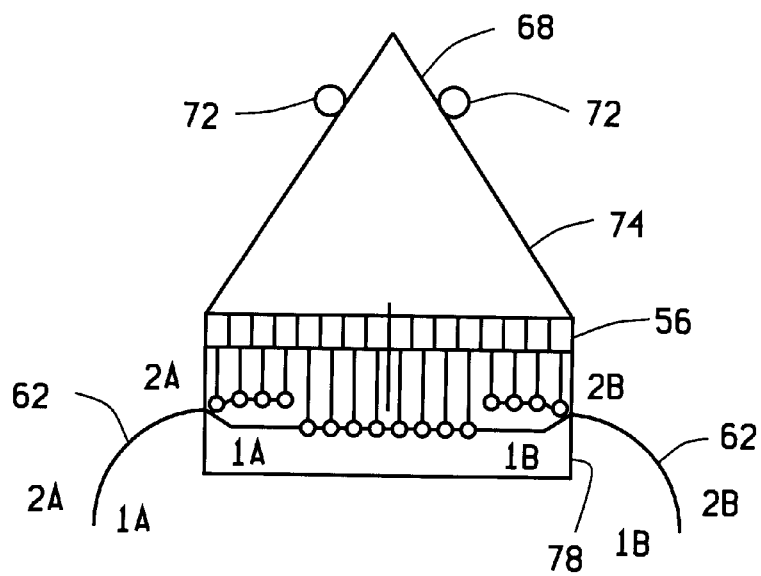
FIGS. 11, 12 and 13 schematically illustrate collection of scan data for various number of slices and slice thicknesses.
Figure 12:
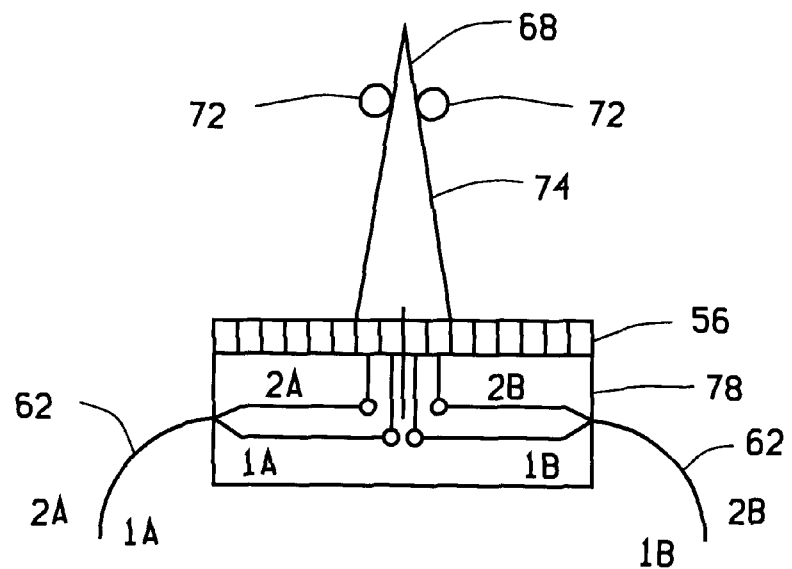

For four slices of data with a 1.25 mm slice thickness, the detector configuration shown in FIG. 12 may be utilized. Particularly, cams 72 are not separated as wide apart as for the 5.0 mm slice thickness (FIG. 11). Rather, cams 72 are separated in the z-axis direction to provide 5 mm collimation, and the photodiode outputs are combined by switching array 78 into four separate slices. Particularly, each slice of data combines the outputs of one photodiodes into one signal (1A, 2A, 1B, and 2B), and each slice data signal (1A, 2A, 1B, and 2B) is supplied to SDAS 42 via flex cables 62.

Figure 13:
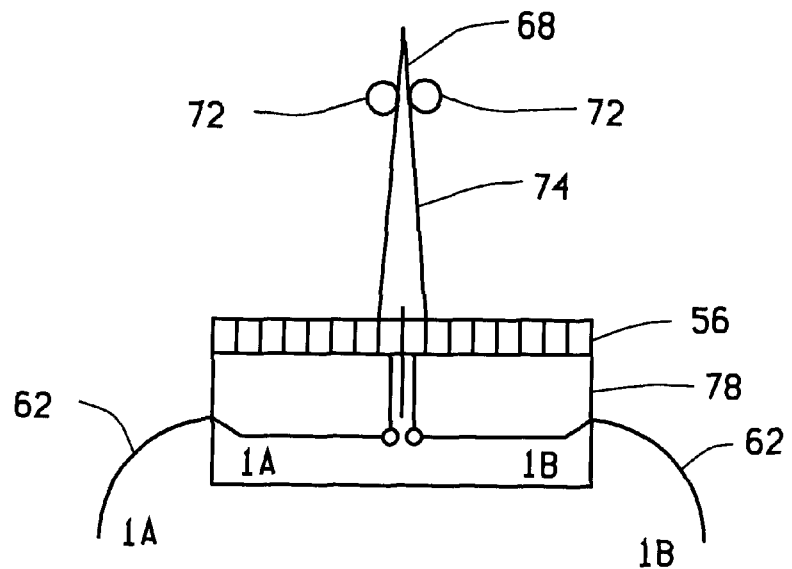

Of course, many other combinations of slice number and slice thickness are possible using system 10. For example, and referring to FIG. 13, for two slices of data with a 1.25 mm slice thickness, cams 72 are separated in the z-axis direction to provide 2.5 mm collimation. The photodiode outputs are combined by switching array 78 into two separate slices. Particularly, each slice of data combines the outputs of one photodiode into one signal (1A and 1B), and each slice data signal (1A and 1B) is supplied to SDAS 42 via flex cables 62. By controlling cam collimator 48 and channel summation along the z-axis as described above, scan data can be collected for many different slice numbers and slice thicknesses.

Many variations and additions to the above described exemplary system can be made. For example, a graphic based user interface which enables the user to easily prescribe multislice scan and image reconstruction in various forms with, for example, optimum table speed, x-ray beam collimation, data collection slice thickness, x-ray beam voltage and current values, as well as the reconstruction method to obtain the desired image quality. Such an interface may be activated by a touch screen, voice, or other known interface methodologies that are easy to use and understand. The host computer can be preprogrammed to include various default modes based upon the type of scan being performed to further simplify the operator performed selections.

Again, the above described multislice CT system can be used to collect one, two or more slices of data to provide enhanced flexibility. Such system also enables fast scanning speed with good image quality and z-axis resolution, with a low x-ray tube load. Further, and using the system, the operator can easily and quickly prescribe multislice scan and image reconstruction parameters.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for generating an image in a scalable multi-slice computed tomography system, said method comprising the steps of:
   performing a scan based on at least one selected scan parameter; and
   retrospectively reconstructing an image using the stored scan data,
   wherein the scan parameter comprises a first slice thickness and wherein the image reconstruction reconstructs an image having a second slice thickness, and wherein the first slice thickness is different from the second slice thickness.

2. A method in accordance with claim 1 wherein the scan parameter comprises table speed.

3. A method in accordance with claim 1 wherein the scan parameter for the helical scan comprises a high image quality scan mode.

4. A method in accordance with claim 1 wherein the scan parameter for the helical scan comprises a high speed scan mode.

5. A method in accordance with claim 1 wherein the scan parameter for the helical scan comprises at least one of a scan speed, a high image quality scan mode, and a high speed scan mode.

6. In a scalable multi-slice computed tomography system, a user interface configured for enabling a user to select at least one scalable scan parameters including a first slice thickness, and for enabling a user to select a second slice thickness for image reconstruction, said second slice thickness being different from said first slice thickness.

7. An interface in accordance with claim 6 wherein said scan parameter comprises slice thicknesses for multiple slice scans.

8. An interface in accordance with claim 6 wherein said scan parameter for a helical scan comprises a scan speed.

9. An interface in accordance with claim 6 wherein said scan parameter for a helical scan comprises a high image quality scan mode.

10. An interface in accordance with claim 6 wherein said scan parameter for a helical scan comprises a high speed scan mode.

11. An interface in accordance with claim 6 wherein said scan parameter for a helical scan comprises a scan speed, a high image quality scan mode, and a high speed scan mode.

12. An interface in accordance with claim 6 wherein said scan parameter for an axial scan further comprises a number of images per rotation.

13. A method for generating an image in a scalable multi-slice computed tomography system, said method comprising the steps of:
   performing a scan based on at least one selected scan parameter;
   collecting multislice scan data by performing a scan based at least in part on the scan parameter; and
   retrospectively reconstructing images corresponding to a first anatomy area in accordance with a first reconstruction option; and
   reconstructing images corresponding to a second anatomy area in accordance with a second reconstruction option.

14. A method for generating an image in a scalable multi-slice in accordance with claim 13 wherein the first reconstruction option is a first slice thickness and the second reconstruction option is a second slice thickness.

15. A method for generating an image in a scalable multi-slice in accordance with claim 13 wherein the first slice thickness and the second slice thickness are different.

* * * * *